(12) United States Patent
Iwaisako et al.

(10) Patent No.: US 9,282,880 B2
(45) Date of Patent: Mar. 15, 2016

(54) WIRELESS POWER SUPPLY APPARATUS, POWER TRANSMISSION COIL UNIT, AND WIRELESS POWER SUPPLY SYSTEM

(75) Inventors: Hiroshi Iwaisako, Shiojiri (JP); Ken Sato, Nagano (JP); Naohito Doi, Nagano (JP); Youhei Sakai, Ina (JP)

(73) Assignee: OLYMPUS CORPORATION, Tokyo (JP)

( * ) Notice: Subject to any disclaimer, the term of this patent is extended or adjusted under 35 U.S.C. 154(b) by 1010 days.

(21) Appl. No.: 13/106,254

(22) Filed: May 12, 2011

(65) Prior Publication Data

US 2011/0210621 A1    Sep. 1, 2011

Related U.S. Application Data

(63) Continuation of application No. PCT/JP2009/068421, filed on Oct. 27, 2009.

(30) Foreign Application Priority Data

Nov. 17, 2008 (JP) .................. 2008-293666
Nov. 17, 2008 (JP) .................. 2008-293667

(51) Int. Cl.
*H01F 27/42* (2006.01)
*A61B 1/04* (2006.01)
*A61B 1/00* (2006.01)
*H02J 5/00* (2006.01)

(52) U.S. Cl.
CPC ............. *A61B 1/041* (2013.01); *A61B 1/00029* (2013.01); *H02J 5/005* (2013.01)

(58) Field of Classification Search
USPC ............. 307/104; 623/16.11, 18.11; 600/424, 600/101; 607/60, 48
See application file for complete search history.

(56) References Cited

U.S. PATENT DOCUMENTS

| | | | |
|---|---|---|---|
| 2007/0167743 A1* | 7/2007 | Honda et al. ................... | 600/424 |
| 2007/0265496 A1 | 11/2007 | Kawano et al. | |
| 2007/0299483 A1* | 12/2007 | Strother et al. ................. | 607/48 |
| 2008/0177133 A1* | 7/2008 | Sakai et al. ..................... | 600/101 |
| 2008/0294258 A1* | 11/2008 | Revie et al. ................ | 623/16.11 |

FOREIGN PATENT DOCUMENTS

| | | |
|---|---|---|
| EP | 1 932 463 A1 | 6/2008 |
| JP | 2001-231186 | 8/2001 |
| JP | 2004-159456 | 6/2004 |
| JP | 2005-287888 | 10/2005 |
| JP | 2005-304638 | 11/2005 |
| JP | 2007-175448 | 7/2007 |
| JP | 2007-195961 | 8/2007 |
| JP | 4089778 | 3/2008 |
| JP | 2008-178544 | 8/2008 |

OTHER PUBLICATIONS

European Search Report dated Apr. 17, 2012 from corresponding European Patent Application No. EP 09 82 6021.9.

* cited by examiner

*Primary Examiner* — Rexford Barnie
*Assistant Examiner* — Jagdeep Dhillon
(74) *Attorney, Agent, or Firm* — Scully, Scott, Murphy & Presser, PC

(57) ABSTRACT

A wireless power supply apparatus for a capsule-type endoscope has three sets of coils that generate a magnetic field in directions that are orthogonal to each other, a gravity sensor that detects a gravitational direction, a coil selection section that selects a coil that generates a magnetic field in a gravitational direction that is detected by the gravity sensor, and a drive section that applies a current to the coil that the coil selection section selects.

15 Claims, 11 Drawing Sheets

FIG.6

| | Pattern 1 | Pattern 2 | Pattern 3 | Pattern 4 | Pattern 5 | Pattern 6 | Pattern 7 | Pattern 8 | Pattern 9 | Pattern 10 | Pattern 11 | Pattern 12 | Pattern 13 |
|---|---|---|---|---|---|---|---|---|---|---|---|---|---|
| SW70a | ON | OFF | OFF | ON | ON | ON | ON | OFF | OFF | ON | ON | ON | ON |
| SW70b | ON | OFF | OFF | OFF | OFF | OFF | OFF | OFF | OFF | OFF | OFF | OFF | OFF |
| SW70c | OFF | ON | OFF | OFF | ON | OFF | OFF | ON | ON | OFF | OFF | ON | ON |
| SW70d | OFF | ON | OFF | ON | OFF | OFF | ON | OFF | OFF | OFF | OFF | OFF | OFF |
| SW70e | OFF | OFF | ON | OFF | OFF | OFF | OFF | ON | ON | ON | ON | OFF | OFF |
| SW70f | OFF | OFF | ON | OFF | OFF | ON | OFF | OFF | OFF | ON | OFF | OFF | OFF |
| SW70g | OFF | OFF | NC | ON | OFF | OFF | OFF | OFF | OFF | OFF | OFF | OFF | OFF |
| SW70h | OFF | OFF | NC | OFF | ON | OFF | OFF | ON | OFF | OFF | OFF | OFF | ON |
| SW70i | NC | OFF | OFF | OFF | OFF | OFF | OFF | OFF | ON | OFF | ON | ON | OFF |
| SW70j | NC | OFF | OFF | OFF | OFF | ON | OFF | OFF | OFF | OFF | OFF | ON | OFF |
| SW70k | OFF | NC | OFF | OFF | OFF | OFF | OFF | OFF | OFF | OFF | OFF | OFF | OFF |
| SW70m | OFF | NC | OFF | OFF | OFF | OFF | ON | OFF | OFF | OFF | OFF | OFF | ON |
| Driving axis | X | Y | Z | X,Y | X,Y | X,Z | X,Z | Y,Z | Y,Z | X,Y,Z | X,Y,Z | X,Y,Z | X,Y,Z |
| Direction of magnetic field | (X+)⇔(X−) | (Y+)⇔(Y−) | (Z+)⇔(Z−) | (X+,Y+)⇔(X−,Y−) | (X+,Y−)⇔(X−,Y+) | (X+,Z+)⇔(X−,Z−) | (X+,Z−)⇔(X−,Z+) | (Y+,Z+)⇔(Y−,Z−) | (Y+,Z−)⇔(Y−,Z+) | (X+,Y+,Z+)⇔(X−,Y−,Z−) | (X+,Y+,Z−)⇔(X−,Y−,Z+) | (X+,Y−,Z+)⇔(X−,Y+,Z−) | (X+,Y−,Z−)⇔(X−,Y+,Z+) |

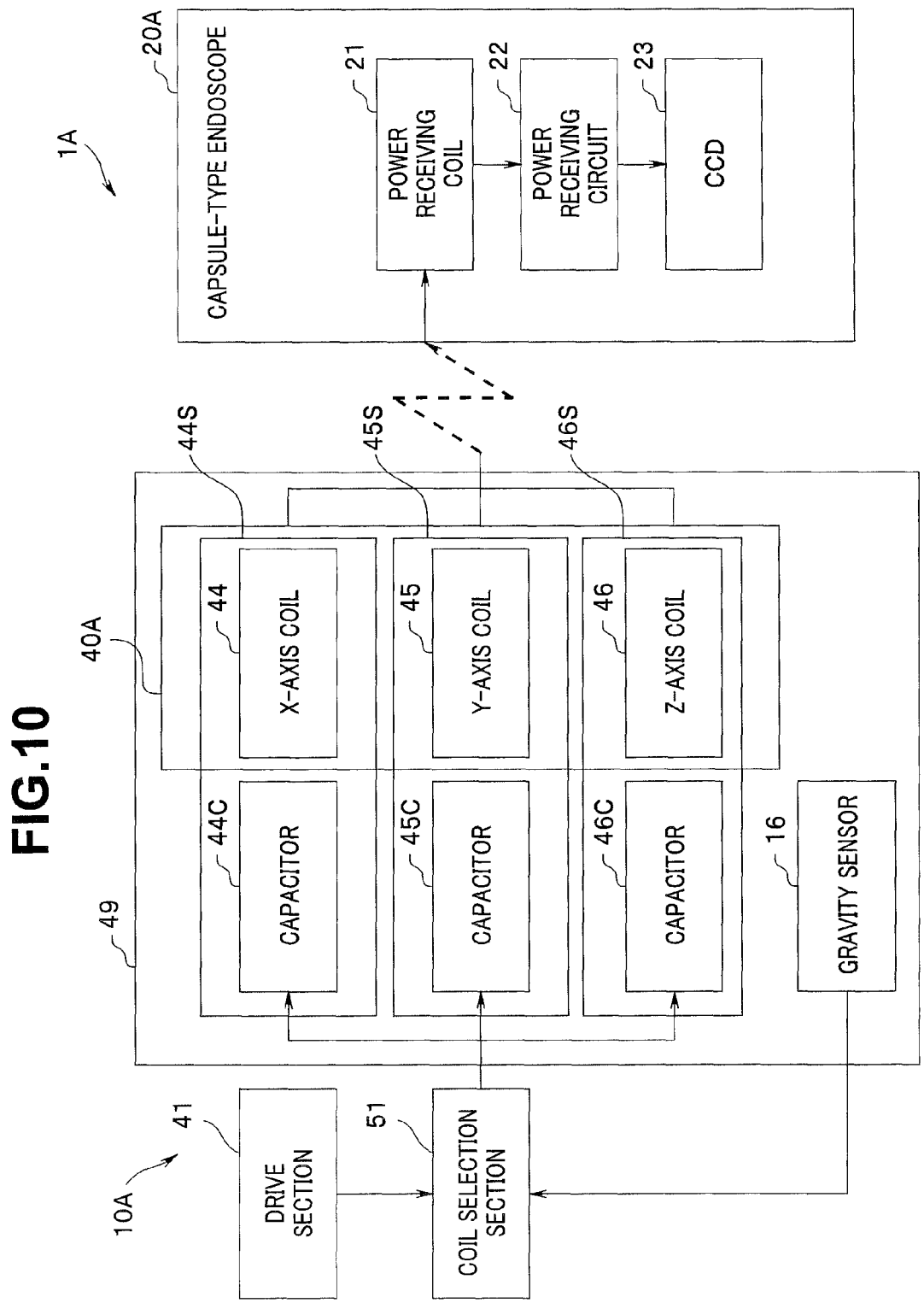

WIRELESS POWER SUPPLY APPARATUS, POWER TRANSMISSION COIL UNIT, AND WIRELESS POWER SUPPLY SYSTEM

CROSS REFERENCE TO RELATED APPLICATION

This application is a continuation application of PCT/JP2009/068421 filed on Oct. 27, 2009 and claims benefit of Japanese Applications No. 2008-293666 filed in Japan on Nov. 17, 2008 and No. 2008-293667 filed in Japan on Nov. 17, 2008, the entire contents of which are incorporated herein by this reference.

BACKGROUND OF INVENTION

1. Field of the Invention

The present invention relates to a wireless power supply apparatus that supplies electric power from outside a subject to a capsule-type medical device that has been introduced into the subject, a power transmission coil unit of the wireless power supply apparatus, and a wireless power supply system that includes the capsule-type medical device and the wireless power supply apparatus.

2. Description of the Related Art

Recently, a capsule-type endoscope (hereunder, also referred to simply as "endoscope") that includes an image pickup function and a wireless function has appeared in the field of endoscopes. The capsule-type endoscope has a configuration such that, after being swallowed by an individual to be examined that is a subject for observation (examination), the endoscope travels through the inside of internal organs such as the stomach and small intestine following the peristaltic movement thereof until being naturally excreted from the body of the individual to be examined. While the endoscope travels through the inside of the internal organs, the endoscope sequentially picks up images of the inside of the internal organs using the image pickup function.

Further, image data that is picked up inside the individual to be examined by the endoscope while traveling through the internal organs is sequentially transmitted to an external apparatus that is provided outside the individual to be examined by means of a wireless function such as wireless communication and stored in a memory. Because the individual to be examined can carry the external apparatus including the wireless function and the memory function, the individual can carry out daily activities without any inconvenience during the observation period from the time of swallowing the endoscope until excretion thereof. After the observation by the endoscope ends, a physician can display images of the internal organs on a displaying section such as a display and make a diagnosis on the basis of image data that is stored in the memory of the external apparatus.

A system that supplies electric power to a capsule-type endoscope is disclosed, for example, in Japanese Patent Application Laid-Open Publication No. 2001-231186. According to the aforementioned system, since a radio capsule (corresponds to a capsule-type endoscope) is kept inside an individual to be examined, electric power is supplied to the inside of the endoscope by transmitting power to inside the endoscope from the outside of the individual to be examined. According to this system, a power transmission coil that is a power transmitting antenna is provided in an external apparatus and a power receiving coil that is a power receiving antenna is provided inside the endoscope. The external apparatus supplies power into the endoscope through the transmitting antenna and the receiving antenna to thereby enable observation operations of the capsule-type endoscope that is kept for an extended period of time inside the individual to be examined.

Further, Japanese Patent Application Laid-Open Publication No. 2004-159456 discloses an energy supply apparatus that is equipped with a plurality of power transmission coils that are disposed so as to generate a magnetic field parallel to each axis (X-axis, Y-axis, and Z-axis) of a three-dimensional orthogonal coordinate system surrounding an individual to be examined, and a power supply apparatus that supplies an electric current that changes in predetermined cycles to the plurality of power transmission coils. The aforementioned energy supply apparatus also has an energy supply amount detection section that detects an amount of energy being supplied to the plurality of power transmission coils, respectively; a detection section that detects a power transmission coil to which a supplied amount of energy is greatest among the plurality of power transmission coils based on a detection result of the energy supply amount detection section; and a selective voltage supply control section that cuts off a voltage supply to a power transmission coil other than the power transmission coil that is detected by the detection section.

According to the configuration of the energy supply apparatus disclosed in Japanese Patent Application Laid-Open Publication No. 2004-159456, the orientations of magnetic fields emitted from power transmission coils are parallel to the respective axes of the three-dimensional orthogonal coordinate system surrounding the individual to be examined. Therefore, for example, if an axial direction of a capsule-type endoscope approximately matches any one of the axial directions of the three-dimensional orthogonal coordinate system that surrounds the individual to be examined, there is a relative increase in the power supply efficiency. In contrast, if, for example, the endoscope is oriented in a direction that corresponds to the middle between each of the axial directions of the three-dimensional orthogonal coordinate system surrounding the individual to be examined, the necessity arises to increase the intensity of a magnetic field emitted from the power transmission coil that is detected by the detection section so that power that is necessary for operations of each section of the endoscope is supplied. As a result, there is a relative decrease in the power supply efficiency.

Consequently, Japanese Patent No. 4089778 discloses a method that detects a degree of coupling between a power receiving coil and a power transmission coil, and drives a power transmission coil that is in a direction in which the degree of coupling is strong.

In this connection, Japanese Patent Application Laid-Open Publication No. 2007-175448 discloses an endoscope that observes a desired observation site by causing a capsule-type endoscope to float in a liquid inside the stomach of an individual to be examined Further, Japanese Patent Application Laid-Open Publication No. 2005-304638 discloses technology that detects a position and an orientation of an endoscope using an exciting coil array for generating a magnetic field from a resonance circuit provided in the endoscope, and a detection coil that detects a magnetic field.

SUMMARY OF THE INVENTION

A wireless power supply apparatus according to an embodiment of the present invention wirelessly supplies power to a capsule-type medical device that is introduced into a body of a subject, wherein: the capsule-type medical device has a power receiving coil that receives an electric power by means of a change in a magnetic field; the wireless power supply apparatus including: three sets of power transmission coils that are arranged on the subject and that generate the magnetic field in directions that are orthogonal to each other, a drive section that applies an electric current to at least one set of the power transmission coils, and a coil selection section that selects the power transmission coils to apply the electric current to in order to cause the power receiving coil of the capsule-type medical device to generate an induced voltage.

A power transmission coil unit according to another embodiment of the present invention is a power transmission coil unit of a wireless power supply apparatus that wirelessly supplies power to a capsule-type medical device that is introduced into a body of a subject, wherein: the capsule-type medical device has a power receiving coil that receives an electric power by means of a change in a magnetic field in a longitudinal direction thereof, and has a structure that enables the capsule-type medical device to float with a longitudinal direction thereof being perpendicular to a surface of a liquid that is retained inside a stomach of the individual to be examined; the power transmission coil unit includes three sets of power transmission coils that generate the magnetic field in directions that are orthogonal to each other, and a gravity sensor that detects a gravitational direction that is arranged on the subject; and the power transmission coil unit is arranged in clothing that the subject wears.

A wireless power supply system according to a further embodiment of the present invention includes a capsule-type medical device that is introduced into a body of a subject, and a wireless power supply apparatus that wirelessly supplies power to the capsule-type medical device, wherein: the capsule-type medical device is a capsule-type endoscope that has a power receiving coil that receives an electric power by means of a change in a magnetic field, and has an image pickup section that is arranged at an end portion in a longitudinal direction; and the wireless power supply apparatus includes: a power transmission coil unit that is arranged on the subject and that has three sets of power transmission coils that generate the magnetic field in directions that are orthogonal to each other, a drive section that applies an electric current to at least one set of the power transmission coils, and a coil selection section that selects the power transmission coils to apply the electric current to in order to generate a magnetic field in a longitudinal direction of the capsule-type medical device.

BRIEF DESCRIPTION OF THE DRAWINGS

FIG. 6 is a view that shows an example of a table that is used when the coil selection section of the wireless power supply apparatus of the first embodiment performs control;

FIG. 10 is a configuration diagram that illustrates a configuration of a wireless power supply system according to a second embodiment; and Each of FIG. 11A to FIG. 13B is a cross-sectional schematic diagram for explaining a relationship between a posture of an individual to be examined and a posture of a capsule-type endoscope;

DETAILED DESCRIPTION OF THE PREFERRED EMBODIMENT(S)

<First Embodiment>

Figure 1:
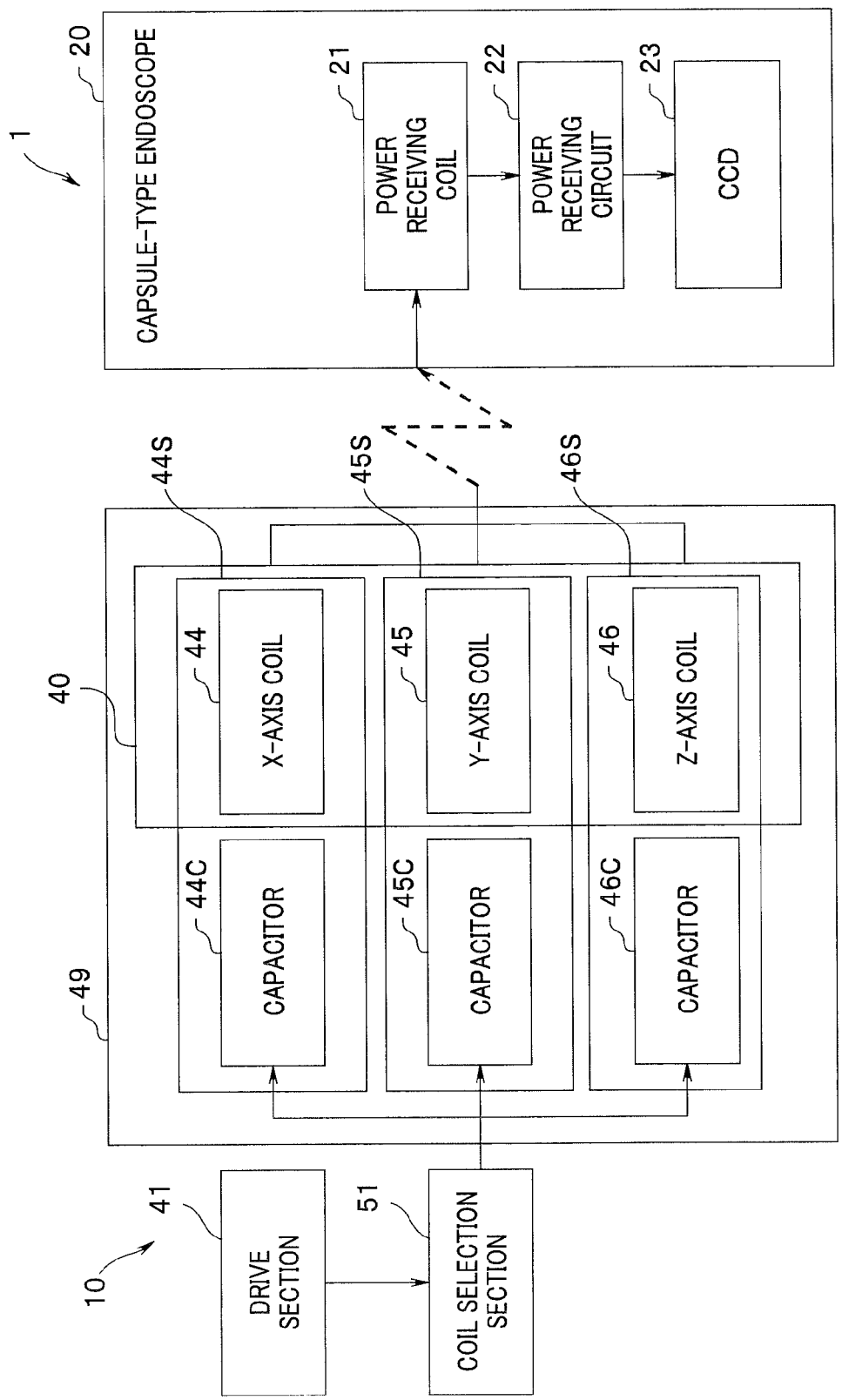
FIG. 1 is a configuration diagram that illustrates a configuration of a wireless power supply system according to a first embodiment.

As shown in FIG. 1, a wireless power supply system 1 of the present embodiment includes a capsule-type endoscope (hereunder, also referred to as "endoscope") 20 that has a CCD 23 and which is a capsule-type medical device that is introduced into the body of an individual to be examined 39 as a subject, and a wireless power supply apparatus 10 that is provided outside the individual to be examined 39. The endoscope 20 receives an AC magnetic field that is generated by a power transmission coil unit 49 by means of a power receiving coil 21, and converts the AC magnetic field into electric power for operation by means of a power receiving circuit 22. The wireless power supply apparatus 10 has the power transmission coil unit 49 that has a power transmission antenna 40 composed of three sets of Helmholtz coils 44, 45, and 46, a drive section 41 as drive means that applies a predetermined alternating current to the power transmission coil unit 49, and a coil selection section 51 as coil selection means that switches respective coil selection switches on and off. Hereunder, the respective Helmholtz coils are also referred to as "power transmission coil" or simply "coil".

Figure 2:
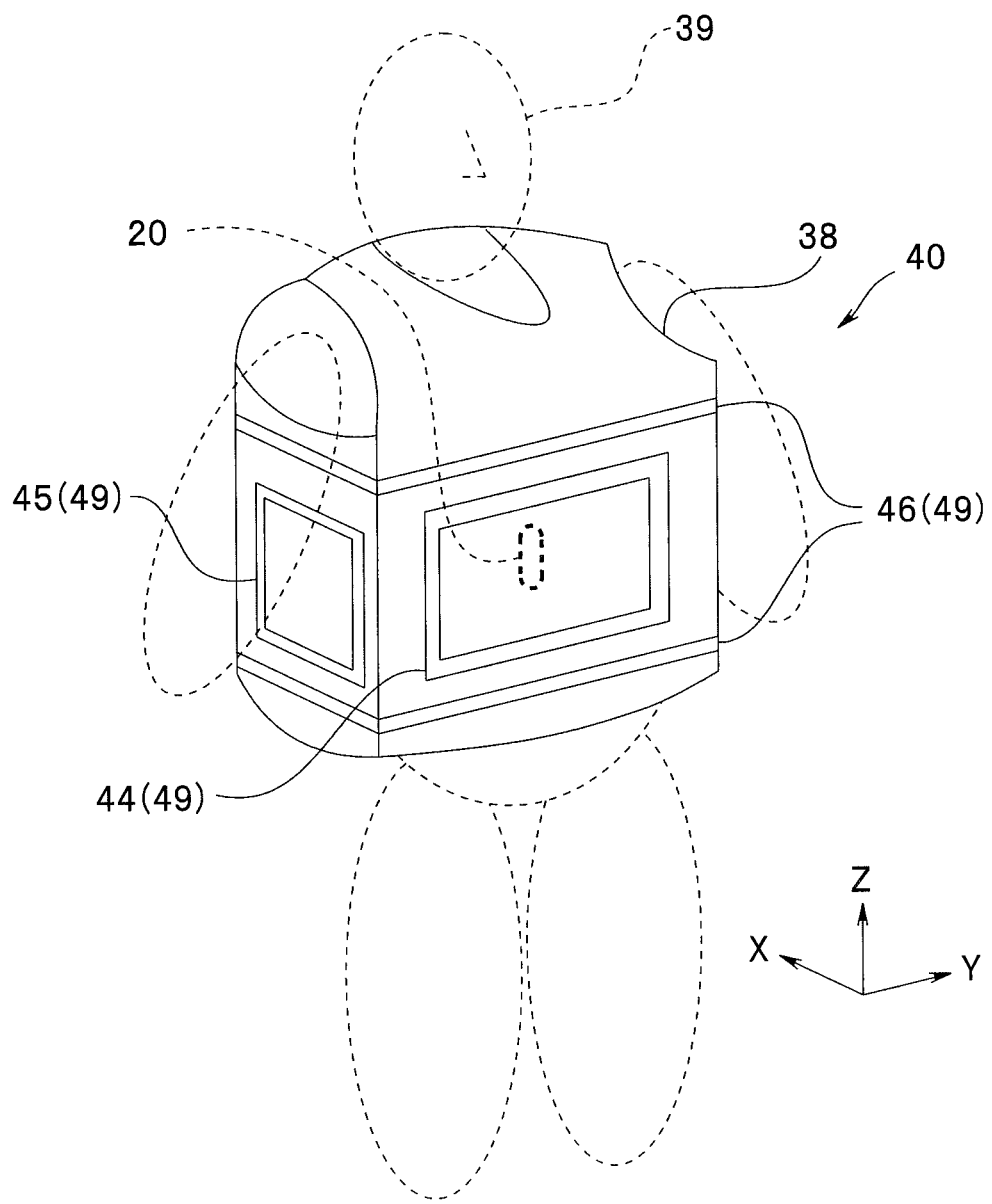
FIG. 2 is an explanatory drawing for describing a usage state of a wireless power supply apparatus of the first embodiment.

First, the power transmission coil unit 49 of the wireless power supply apparatus 10 of the present embodiment will be described. As shown in FIG. 2, the power transmission antenna 40 is arranged in a vest 38 that is clothing that the individual to be examined 39 wears, and includes an X-axis coil 44, a Y-axis coil 45, and a Z-axis coil 46 that generate an AC magnetic field in directions that are orthogonal to each other. The X-axis coil 44 and a capacitor 44C constitute an X-axis coil unit 44S. The Y-axis coil 45 and a capacitor 45C constitute a Y-axis coil unit 45S. The Z-axis coil 46 and a capacitor 46C constitute a Z-axis coil unit 46S. The power transmission coil unit 49 is composed of the X-axis coil unit 44S, the Y-axis coil unit 45S, and the Z-axis coil unit 46S. The endoscope 20 that is introduced into the body of the individual to be examined 39 receives an electric power by means of a change in a magnetic field that the power transmission coil unit 49 generates, that is, by subjecting an AC magnetic field to magneto-electric conversion.

Figure 3:
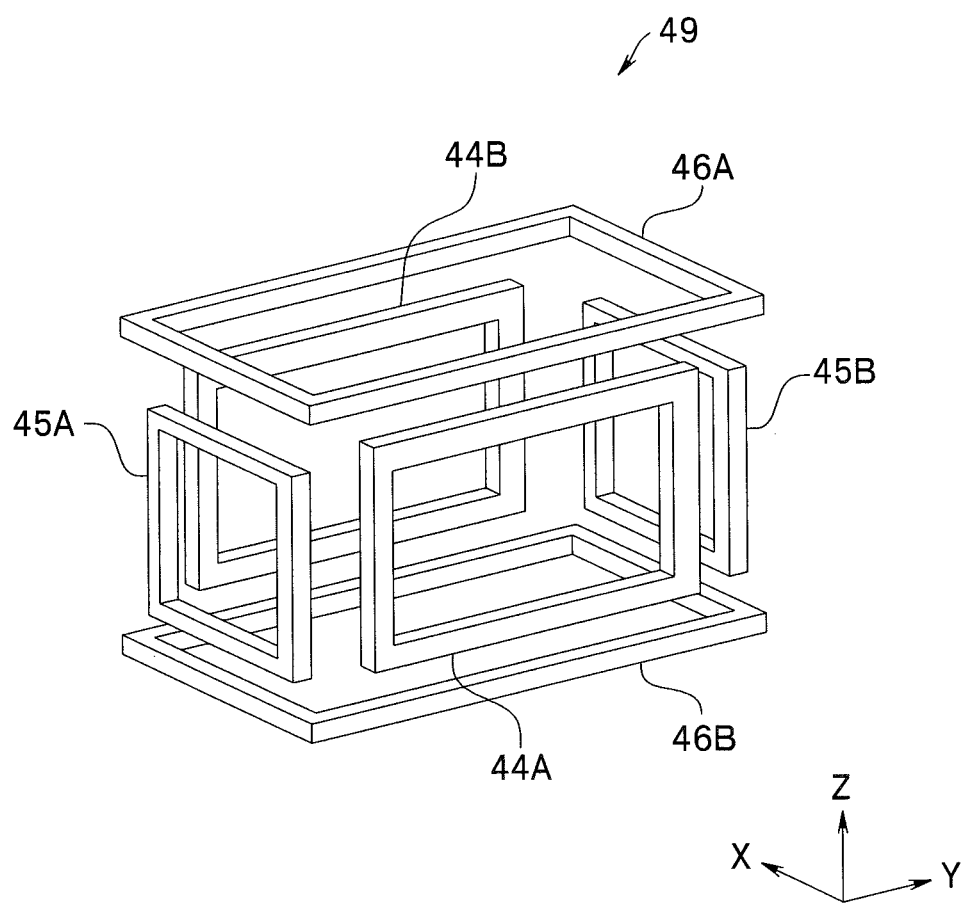
FIG. 3 is a schematic drawing for describing a configuration of a power transmission coil unit of the wireless power supply apparatus of the first embodiment.

As shown in FIG. 2 and FIG. 3, the X-axis coil 44 is composed of a helical coil 44A that is disposed at a front face of the vest 38 and a helical coil 44B that is disposed at a rear face of the vest 38. The X-axis coil 44 generates a magnetic field that is parallel to the X-axis direction. The Y-axis coil 45 is composed of a helical coil 45A that is disposed at a right face of the vest 38 and a helical coil 45B that is disposed at a left face of the vest 38. The Y-axis coil 45 generates a magnetic field that is parallel to the Y-axis direction. The Z-axis coil 46 is composed of a helical coil 46A that is disposed at an upper portion of the vest 38 and a helical coil 46B that is disposed at a lower portion of the vest 38. The Z-axis coil 46 generates a magnetic field that is parallel to the Z-axis direction.

More specifically, when an electric current is applied to the respective power transmission coils, a magnetic field that is parallel to the direction in which the respective coils are facing is generated with respect to the inside of the body of the individual to be examined 39.

Note that although rectangular coils are shown in FIG. 2 and FIG. 3 for the purpose of description, the outer shape of the coils may be circular or elliptical or the like, and the coils may be formed to have a curved surface. The coils may also be flexible coils whose shape can be adjusted to match the outer shape of the individual to be examined 39 or the like. Further, the number of turns of the respective coils 44, 45, and 46 is appropriately selected.

Figure 4:
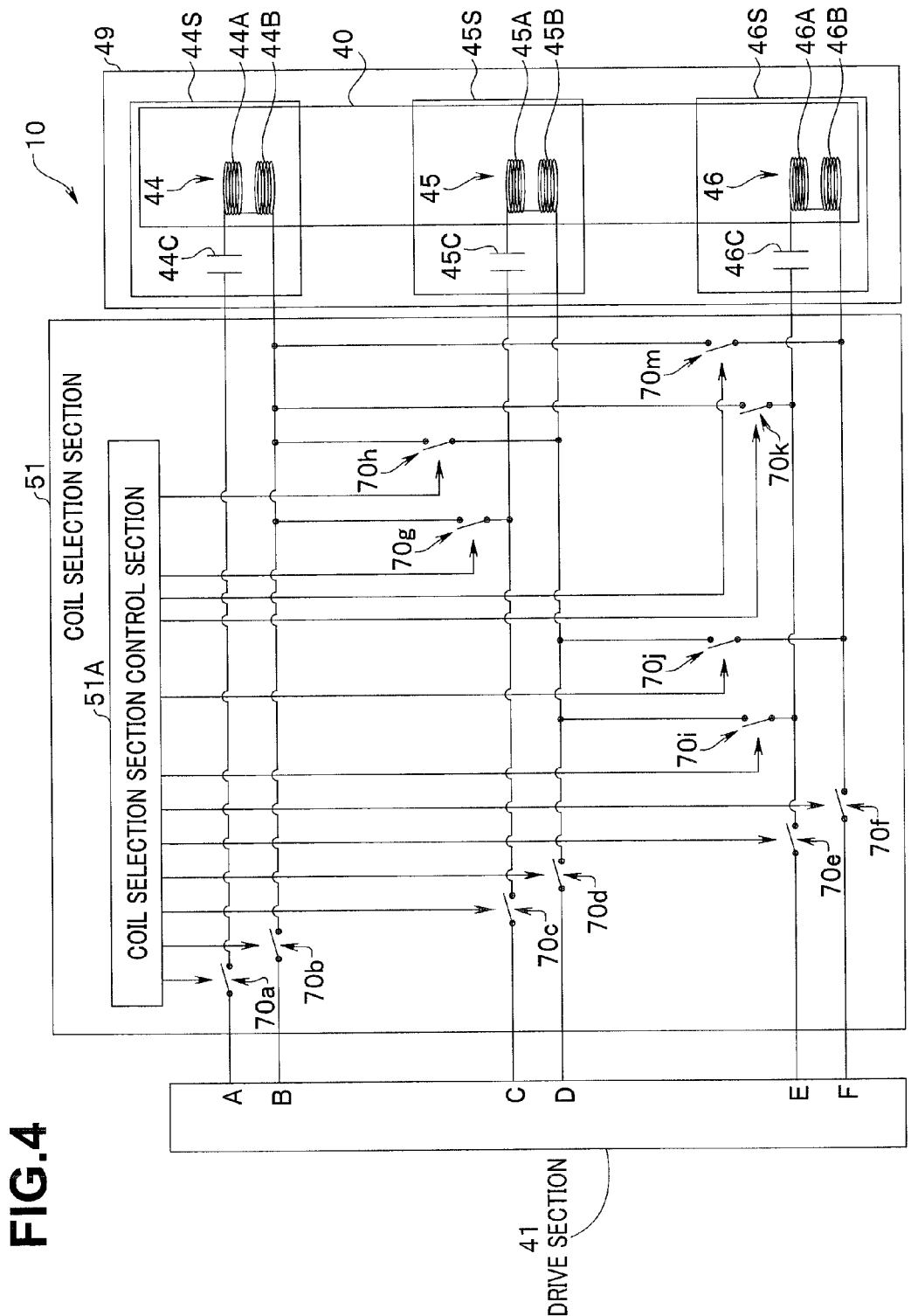
FIG. 4 is an explanatory drawing for describing a coil selection section and the power transmission coil unit of the first embodiment.

Next, the operations of the coil selection section 51 are described in detail using FIG. 4. As described above, the wireless power supply apparatus 10 includes the power transmission coil unit 49 (the X-axis coil 44 disposed along the X-axis, the Y-axis coil 45 disposed along the Y-axis, and the Z-axis coil 46 disposed along the Z-axis in a three-dimensional orthogonal coordinate system that takes the position of the endoscope 20 as an origin), the drive section 41 that applies a predetermined alternating current to the power transmission coil unit 49, and the coil selection section 51 that has respective switches that are described later and that performs switching operations with respect to each switch.

As shown in FIG. 4, the coil selection section 51 has a switch 70a that switches a connection state between a first end portion of the X-axis coil unit 44S and a terminal A of the drive section 41 on or off, a switch 70b that switches a connection state between a second end portion of the X-axis coil unit 44S and a terminal B of the drive section 41 on or off, a switch 70c that switches a connection state between a first end portion of the Y-axis coil unit 45S and a terminal C of the drive section 41 on or off, a switch 70d that switches a connection state between a second end portion of the Y-axis coil unit 45S and a terminal D of the drive section 41 on or off, a switch 70e that switches a connection state between a first end portion of the Z-axis coil unit 46S and a terminal E of the drive section 41 on or off, a switch 70f that switches a connection state between a second end portion of the Z-axis coil unit 46S and a terminal F of the drive section 41 on or off, and a coil selection section control section 51A that performs control of the coil selection section.

Furthermore, the coil selection section 51 has a switch 70g that switches a connection state between the second end portion of the X-axis coil unit 44S and the first end portion of the Y-axis coil unit 45S on or off, a switch 70h that switches a connection state between the second end portion of the X-axis coil unit 44S and the second end portion of the Y-axis coil unit 45S on or off, a switch 70i that switches a connection state between the second end portion of the Y-axis coil unit 45S and the first end portion of the Z-axis coil unit 46S on or off, a switch 70j that switches a connection state between the second end portion of the Y-axis coil unit 45S and the second end portion of the Z-axis coil unit 46S on or off, a switch 70k that switches a connection state between the second end portion of the X-axis coil unit 44S and the first end portion of the Z-axis coil unit 46S on or off, and a switch 70m that switches a connection state between the second end portion of the X-axis coil unit 44S and the second end portion of the Z-axis coil unit 46S on or off.

More specifically, the coil selection section 51 of the present embodiment has the respective switches 70a to 70m. Further, the coil selection section 51 performs control for switching the respective switches 70a to 70m on or off.

The X-axis coil unit 44S has a configuration in which a resonance capacitor 44C that is connected to its own first end portion side, and a power transmission coil 44 that is connected to its own second end portion side are connected in series. The power transmission coil 44 includes a coil 44A disposed on a positive region (hereafter, referred to as "X+ region") side of the X-axis in the three-dimensional orthogonal coordinate system, and a coil 44B disposed on a negative region (hereafter, referred to as "X− region") side of the X-axis in the three-dimensional orthogonal coordinate system.

In the X-axis coil unit 44S, a capacitance value of the capacitor 44C and an inductance value of a power transmission coil 44 are respectively set so as to be compatible with a predetermined resonance frequency.

The Y-axis coil unit 45S has a configuration in which a resonance capacitor 45C that is connected to its own first end portion side, and a power transmission coil 45 that is connected to its own second end portion side are connected in series. The power transmission coil 45 includes a coil 45A disposed on a positive region (hereafter, referred to as "Y+ region") side of the Y-axis in the three-dimensional orthogonal coordinate system, and a coil 45B disposed on a negative region (hereafter, referred to as "Y− region") side of the Y-axis in the three-dimensional orthogonal coordinate system.

In the Y-axis coil unit 45S, a capacitance value of the capacitor 45C and an inductance value of the power transmission coil 45 are respectively set so as to be compatible with a predetermined resonance frequency.

The Z-axis coil unit 46S has a configuration in which a resonance capacitor 46C that is connected to its own first end portion side, and a power transmission coil 46 that is connected to its own second end portion side are connected in series. The power transmission coil 46 includes a coil 46A disposed on a positive region (hereafter, referred to as "Z+ region") side of the Z-axis in the three-dimensional orthogonal coordinate system, and a coil 46B disposed on a negative region (hereafter, referred to as "Z− region") side of the Z-axis in the three-dimensional orthogonal coordinate system.

In the Z-axis coil unit 46S, a capacitance value of the capacitor 46C and an inductance value of the power transmission coil 46 are respectively set so as to be compatible with a predetermined resonance frequency.

Figure 5:
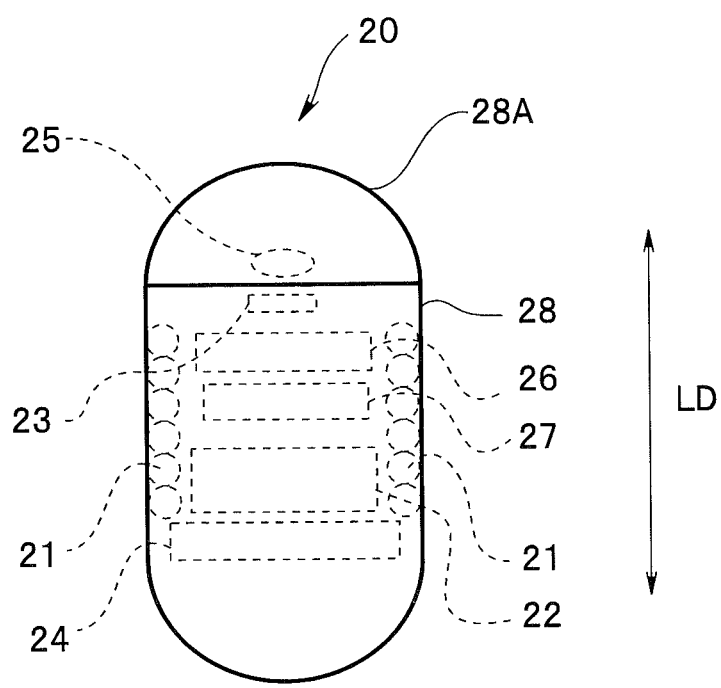
FIG. 5 is a cross-sectional schematic diagram that illustrates a configuration of a capsule-type endoscope of the first embodiment.

In this case, as shown in FIG. 5, the endoscope 20 that is introduced into the body of the individual to be examined 39 has the CCD 23 as image pickup means that is arranged at an end portion in the longitudinal direction, the power receiving coil 21 that receives an electric power by means of a change in a magnetic field in a direction parallel to the longitudinal direction, and the power receiving circuit 22.

More specifically, the endoscope 20 is an elongated capsule shape that has a longitudinal direction (LD) and a transverse direction, in which a cross section in an orthogonal direction to the long axis is approximately circular. The power receiving coil 21 that is of a solenoid type that has a magnetic path in a direction parallel to the long axis is arranged inside a capsule case 28. The power receiving coil 21 receives an electric power by means of an electromagnetic induction effect caused by a change in a magnetic field in the magnetic path direction, that is, a direction parallel to the longitudinal direction (LD) of the endoscope 20. The electric power received by the power receiving coil 21, that is, a current that flows to the power receiving coil as the result of electromagnetic induction, is rectified at the power receiving circuit 22 and serves as power for driving the CCD 23 and the like.

A capsule case portion 28A on the end portion side on which the CCD 23 is arranged is transparent. Images of the inside of the body of the individual to be examined 39 into which the endoscope 20 has been introduced are picked up by the CCD 23 through a lens 25. The images are processed by an image processing circuit 26 and transmitted to outside the body of the individual to be examined 39 via a transmission/reception circuit 27 and an unshown transmission antenna. A secondary battery 24 is disposed on a rear end side that is an opposite side to the end portion side on which the CCD 23 is arranged.

Next, the operations of the wireless power supply apparatus 10 of the present embodiment will be described. Using technology disclosed in Japanese Patent Application Laid-Open Publication No. 2005-304638 or the like, the coil selection section 51 of the wireless power supply apparatus 10 monitors the position and orientation of the endoscope 20 at intervals of a fixed time period and performs control according to the result. In this connection, hereunder a case is described in which the endoscope 20 is at the origin position.

First, a case is described in which the endoscope 20 is facing in a direction approximately along any one axis among three axes of a three-dimensional orthogonal coordinate system.

The coil selection section 51 previously holds information of respective patterns in a table as shown in FIG. 6. Based on a detection result with respect to the position and orientation of the endoscope 20, the coil selection section 51 determines by calculation that the endoscope 20 is, for example as shown in FIG. 7, facing in a direction along the X-axis of the three-dimensional orthogonal coordinate system.

In this connection, the term "facing in a direction along the X-axis" includes a predetermined range and, for example, refers to a range of ±10 degrees with respect to the X-axis. The same applies with respect to a direction of the endoscope 20 in the description hereunder.

The coil selection section 51 switches each of the switches 70a to 70m on or off by selecting an optimal single pattern with respect to the orientation of the endoscope 20 from among the respective patterns.

Figure 7:
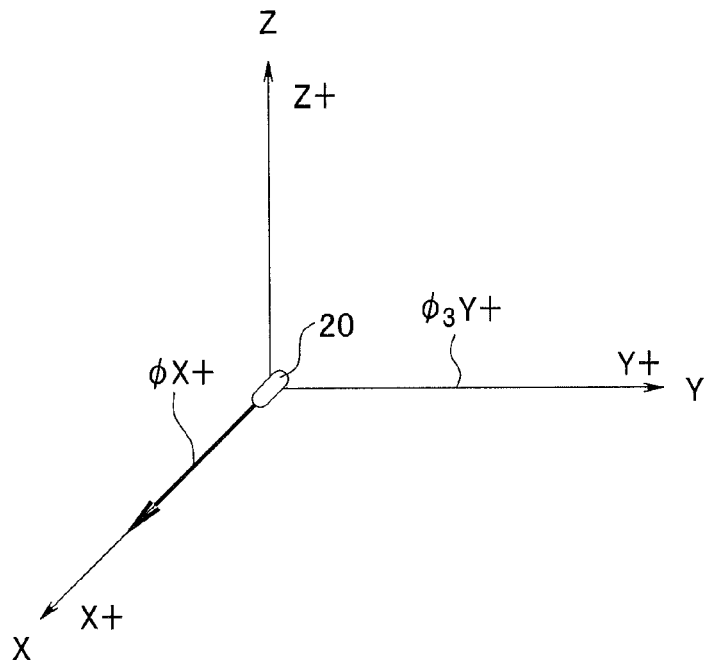
FIG. 7 is a view that illustrates an example in a case where a capsule-type endoscope is facing in a direction that is approximately along any one axis among three axes of a three-dimensional orthogonal coordinate system.

Accordingly, if the coil selection section 51 detects that the endoscope 20 is facing in the direction shown in FIG. 7, the coil selection section 51 selects information of "pattern 1" among the patterns shown in FIG. 6. Based on the information of the selected "pattern 1", the coil selection section 51 performs control to switch on the switches 70a and 70b and switch off the switches 70c to 70f, 70k and 70m. Note that in this case the coil selection section 51 may switch the switches 70i and 70j on or may switch the switches 70i and 70j off (corresponds to "NC (No Care)" in FIG. 6).

In other words, when the coil selection section 51 detects that the endoscope 20 is facing in the direction shown in FIG. 7, the coil selection section 51 selects the X-axis coil 44 as the antenna that is the driving target and performs control with respect to each of the switches 70a to 70m so that the X-axis coil 44 and the drive section 41 are connected in series.

In accordance with the control of the coil selection section 51, an alternating current is applied between the terminal A and the terminal B at the drive section 41. When a current is applied between the terminal A and the terminal B at the drive section 41, the current flows on a path on which the terminal A, the switch 70a, the capacitor 44C, the coil 44A, the coil 44B, the switch 70b and the terminal B are connected in series. As a result, a magnetic field is generated between the X+ region and the X− region.

More specifically, when a current flows in the order of terminal A→switch 70a→capacitor 44C→coil 44A→coil 44B→switch 70b→terminal B, as shown in FIG. 7, a magnetic field ϕX+ is generated along the positive direction of the X-axis. Further, when a current flows in the reverse order to the above order, a magnetic field is generated along the negative direction of the X-axis. The endoscope 20 receives electric power as a result of this change in the magnetic field.

Further, if the coil selection section 51 detects that the endoscope 20 is facing in a direction (not shown) along the Y-axis of the three-dimensional orthogonal coordinate system, the coil selection section 51 selects information of "pattern 2" among the patterns shown in FIG. 6. Based on the information of the selected "pattern 2", the coil selection section 51 performs control to switch on the switches 70c and 70d and switch off the switches 70a, 70b, and 70e to 70j. Note that in this case the coil selection section 51 may switch the switches 70k and 70m on or may switch the switches 70k and 70m off (corresponds to "NC (No Care)" in FIG. 6).

In accordance with the control of the coil selection section 51, an alternating current is applied between the terminal C and the terminal D at the drive section 41. When a current is applied between the terminal C and the terminal D at the drive section 41, the current flows on a path on which the terminal C, the switch 70c, the capacitor 45C, the coil 45A, the coil 45B, the switch 70d and the terminal D are connected in series. As a result, a magnetic field is generated between the Y+ region and the Y− region.

More specifically, when a current flows in the order of terminal C→switch 70c→capacitor 45C→coil 45A→coil 45B→switch 70d→terminal D, a magnetic field ϕY+ is generated along the positive direction of the Y-axis. Further, when a current flows in the reverse order to the above order, a magnetic field is generated along the negative direction of the Y-axis.

In contrast, when the coil selection section 51 detects that the endoscope 20 is facing in a direction (not shown) along the Z-axis of the three-dimensional orthogonal coordinate system, the coil selection section 51 selects information of "pattern 3" from among the patterns shown in FIG. 6. Based on the information of the selected "pattern 3", the coil selection section 51 performs control to switch on the switches 70e and 70f and switch off the switches 70a to 70d and 70i to 70m. Note that in this case the coil selection section 51 may switch the switches 70g and 70h on or may switch the switches 70g and 70h off (corresponds to "NC (No Care)" in FIG. 6).

In accordance with the control of the coil selection section 51, an alternating current is applied between the terminal E and the terminal F at the drive section 41. When a current is applied between the terminal F and the terminal F at the drive section 41, the current flows on a path on which the terminal E, the switch 70e, the capacitor 46C, the coil 46A, the coil 46B, the switch 70f and the terminal F are connected in series. As a result, a magnetic field is generated between the Z+ region and the Z− region.

More specifically, when a current flows in the order of terminal E→switch 70e→capacitor 46C→coil 46A→coil 46B→switch 70f→terminal F, a magnetic field ϕZ+ is generated along the positive direction of the Z-axis. Further, when a current flows in the reverse order to the above order, a magnetic field is generated along the negative direction of the Z-axis.

In this connection, when "pattern 1" is selected from among the respective patterns shown in FIG. 6, an electric power $P_{X1}$ that is consumed at the wireless power supply apparatus 10 in order to generate a magnetic field $\phi_c$ of an intensity required for operation of the endoscope 20 is shown by the following equation (1).

Equation 1

$$P_{X1} = I_{X1} \times V_{X1} = I_{X1}^2 \times Z_{X1} \qquad (1)$$

In the above equation (1), $I_{X1}$ represents the current required in order to generate the magnetic field $\phi_c$, $V_{X1}$ represents a voltage applied in order to cause the current $I_{X1}$ to flow, and $Z_{X1}$ represents the impedance of the X-axis coil unit 44S. Further, the above equation (1) can be similarly applied in a case where "pattern 2" or "pattern 3" in FIG. 6 is selected, respectively.

Next, a case is described in which the endoscope 20 is facing in a direction that corresponds to the middle between any two axes among the three axes of the three-dimensional orthogonal coordinate system.

Figure 8:
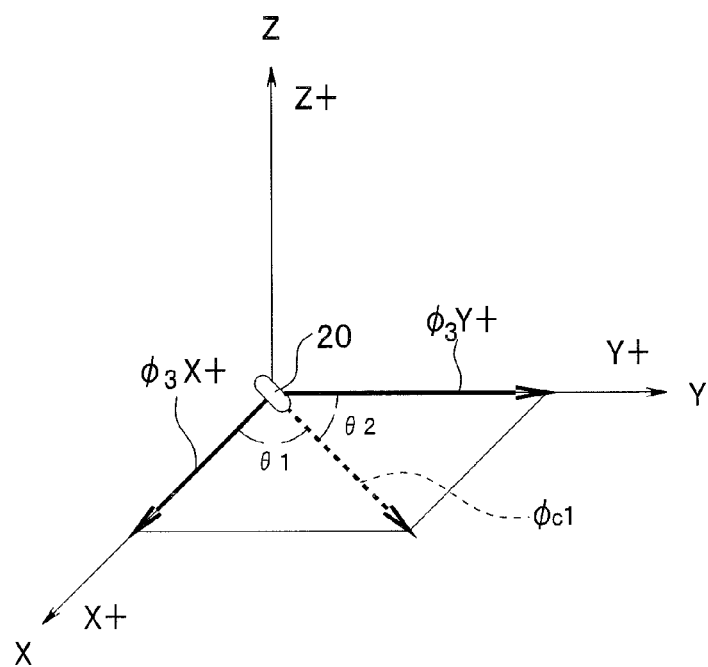
FIG. 8 is a view that illustrates an example in a case where a capsule-type endoscope is facing in a direction that corresponds to the middle between any two axes among three axes of a three-dimensional orthogonal coordinate system.

First, based on the detection result with respect to the orientation of the endoscope 20, the coil selection section 51 determines by calculation that the endoscope 20 is facing in a direction that corresponds to the middle between the X-axis and Y-axis of the three-dimensional orthogonal coordinate system. More specifically, based on the detection result with respect to the orientation of the endoscope 20, the coil selection section 51, for example, determines by calculation that, as shown in FIG. 8, end portions in the longitudinal direction of the endoscope 20 are respectively present in a first quadrant and a third quadrant on a plane that is horizontal to the XY plane of the three-dimensional orthogonal coordinate system, that an angle $\theta_1$ is formed between the endoscope 20 and the X-axis, and that an angle $\theta_2$ is formed between the endoscope 20 and the Y-axis. In this connection, hereunder an example is described for a case where $\theta_1 = \theta_2 = 45°$.

When the coil selection section 51 detects that the endoscope 20 is facing in the direction shown in FIG. 8, the coil selection section 51 selects the information of "pattern 4" from among the patterns shown in FIG. 6.

Based on the information of the selected "pattern 4", the coil selection section 51 performs control to switch on the switches 70a, 70d, and 70g and switch off the switches 70b, 70c, 70e, 70f and 70h to 70m.

In other words, when the coil selection section 51 detects that the endoscope 20 is facing in the direction shown in FIG. 8, the coil selection section 51 selects the coils 44 and 45 as antennas that are the driving targets, and performs control with respect to each of the switches 70a to 70m so that the coils 44 and 45 and the drive section 41 are connected in series.

In accordance with the control of the coil selection section 51, an alternating current is applied between the terminal A and the terminal D at the drive section 41. When a current is applied between the terminal A and the terminal D at the drive section 41, the current flows on a path on which the terminal A, the switch 70a, the capacitor 44C, the coil 44A, the coil 44B, the switch 70g, the capacitor 45C, the coil 45A, the coil 45B, the switch 70d and the terminal D are connected in series. As a result, a magnetic field is generated between a region corresponding to a middle region between the X+ region and Y+ region and a region corresponding to a middle region between the X− region and the Y− region.

More specifically, when a current flows in the order of terminal A→switch 70a→capacitor 44C→coil 44A→coil 44B→switch 70g→capacitor 45C→coil 45A→coil 45B→switch 70d→terminal D, as shown in FIG. 8, a combined magnetic field $\phi_{c1}$ is generated by a magnetic field $\phi_3 X+$ along the positive direction of the X-axis and a magnetic field $\phi_3 Y+$ along the positive direction of the Y-axis. Further, when a current flows in the reverse order to the above order, a combined magnetic field is generated in the opposite direction to the combined magnetic field $\phi_{c1}$.

More specifically, when the coil selection section 51 selects "pattern 4", since the coil 44A, the coil 44B, the coil 45A, and the coil 45B are connected in series, a current of the same size flows to each coil. In such a case, an electric power $P_{XY}$ that is consumed at the wireless power supply apparatus 10 is shown by the following equation (2).

Equation 2

$$P_{XY} = I_{XY}^2 \times Z_{XY} \qquad (2)$$

In the above equation (2), $I_{XY}$ represents the current required in order to generate the combined magnetic field $\phi_{c1}$, and $Z_{XY}$ represents a combined impedance of the X-axis coil unit 44S and the Y-axis coil unit 45S.

In this case, if it is assumed that the size of the combined magnetic field $\phi_{c1}$ is equal to the size of the aforementioned magnetic field $\phi_c$, and that $\theta_1 = \theta_2 = 45°$, when "pattern 4" is selected by the coil selection section 51, the intensity of the magnetic field $\phi_3 X+$ and the intensity of the magnetic field $\phi_3 Y+$ become equal as shown by the following equation (3).

Equation 3

$$\phi_3 X+ = \phi_3 Y+ = \phi_c \times 1/\sqrt{2} \qquad (3)$$

Therefore, the size of a current $I_{XY}$ that flows to the coil 44A, the coil 44B, the coil 45A, and the coil 45B that are connected in series is shown by the following equation (4).

Equation 4

$$I_{XY} = I_{X1} \times 1/\sqrt{2} \qquad (4)$$

In addition, when it is assumed that the impedance of the Y-axis coil unit 45S is equal to the impedance of the X-axis coil unit 44S ($Z_{X1}$), the above described equation (2) accordingly changes into equation (5) below.

Equation 5

$$\begin{aligned} P_{XY} &= I_{XY}^2 \times Z_{XY} \\ &= \left(I_{X1} \times 1/\sqrt{2}\right)^2 \times 2 \times Z_{X1} \\ &= I_{X1}^2 \times Z_{X1} = P_{X1} \end{aligned} \qquad (5)$$

In contrast, when the end portions in the longitudinal direction of the endoscope 20 are present in a second quadrant and a fourth quadrant on a plane that is horizontal to the XY plane of the three-dimensional orthogonal coordinate system, the coil selection section 51 of the wireless power supply apparatus 10 of the present embodiment selects the information of "pattern 5" from among the patterns shown in FIG. 6. In this case, an alternating current is applied between the terminal A and the terminal C of the drive section 41, and the current flows on a path on which the terminal A, the switch 70a, the capacitor 44C, the coil 44A, the coil 44B, the switch 70h, the coil 45B, the coil 45A, the capacitor 45C, the switch 70c and the terminal C are connected in series. As a result, a magnetic field that is in accordance with the current is generated.

Further, when the end portions in the longitudinal direction of the endoscope 20 are present in a first quadrant and a third quadrant on a plane that is horizontal to an XZ plane of the three-dimensional orthogonal coordinate system, the coil selection section 51 selects the information of "pattern 6" from among the patterns shown in FIG. 6. In this case, an alternating current is applied between the terminal A and the terminal F of the drive section 41, and the current flows on a path on which the terminal A, the switch 70*a*, the capacitor 44C, the coil 44A, the coil 44B, the switch 70*k*, the capacitor 46C, the coil 46A, the coil 46B, the switch 70*f* and the terminal F are connected in series. As a result, a magnetic field that is in accordance with the current is generated.

Furthermore, when the end portions in the longitudinal direction of the endoscope 20 are present in a second quadrant and a fourth quadrant on a plane that is horizontal to the XZ plane of the three-dimensional orthogonal coordinate system, the coil selection section 51 selects the information of "pattern 7" from among the patterns shown in FIG. 6. In this case, an alternating current is applied between the terminal A and the terminal E of the drive section 41, and the current flows on a path on which the terminal A, the switch 70*a*, the capacitor 44C, the coil 44A, the coil 44B, the switch 70*m*, the coil 46B, the coil 46A, the capacitor 46C, the switch 70*e* and the terminal E are connected in series. As a result, a magnetic field that is in accordance with the current is generated.

When the end portions in the longitudinal direction of the endoscope 20 are present in a first quadrant and a third quadrant on a plane that is horizontal to a YZ plane of the three-dimensional orthogonal coordinate system, the coil selection section 51 selects the information of "pattern 8" from among the patterns shown in FIG. 6. In this case, an alternating current is applied between the terminal C and the terminal F of the drive section 41, and the current flows on a path on which the terminal C, the switch 70*c*, the capacitor 45C, the coil 45A, the coil 45B, the switch 70*i*, the capacitor 46C, the coil 46A, the coil 46B, the switch 70*f* and the terminal F are connected in series. As a result, a magnetic field that is in accordance with the current is generated.

Further, when the end portions in the longitudinal direction of the endoscope 20 are present in a second quadrant and a fourth quadrant on the plane that is horizontal to the YZ plane of the three-dimensional orthogonal coordinate system, the coil selection section 51 selects the information of "pattern 9" from among the patterns shown in FIG. 6. In this case, an alternating current is applied between the terminal C and the terminal E of the drive section 41, and the current flows on a path on which the terminal C, the switch 70*c*, the capacitor 45C, the coil 45A, the coil 45B, the switch 70*j*, the coil 46B, the coil 46A, the capacitor 46C, the switch 70*e* and the terminal E are connected in series. As a result, a magnetic field that is in accordance with the current is generated.

More specifically, when the wireless power supply apparatus 10 according to the present embodiment selects any one of "pattern 5", "pattern 6", "pattern 7", "pattern 8", and "pattern 9", operations are performed in a similar manner to the operations when the aforementioned "pattern 4" is selected. Consequently, according to the wireless power supply apparatus 10 of the present embodiment, when the same conditions as in the case of the aforementioned "pattern 4" are set, the above described equations (2) to (5) can be similarly applied with respect to any of "pattern 5", "pattern 6", "pattern 7", "pattern 8", and "pattern 9".

As described above, when the longitudinal direction of the endoscope 20 is facing in a direction that corresponds to the middle between any two axes among three axes of the three-dimensional orthogonal coordinate system, the wireless power supply apparatus 10 of the present embodiment serially connects two sets of power transmission coils that are respectively disposed along two axes and causes a current to flow. Therefore, the wireless power supply apparatus 10 of the present embodiment can cause the axial direction of the endoscope 20 and a direction in which a magnetic field is generated to match while suppressing power consumption, and can thus efficiently supply electric power to the endoscope 20.

Next, a case is described in which the endoscope 20 is facing in a direction that corresponds to the middle between all three axes in the three-dimensional orthogonal coordinate system.

Figure 9:
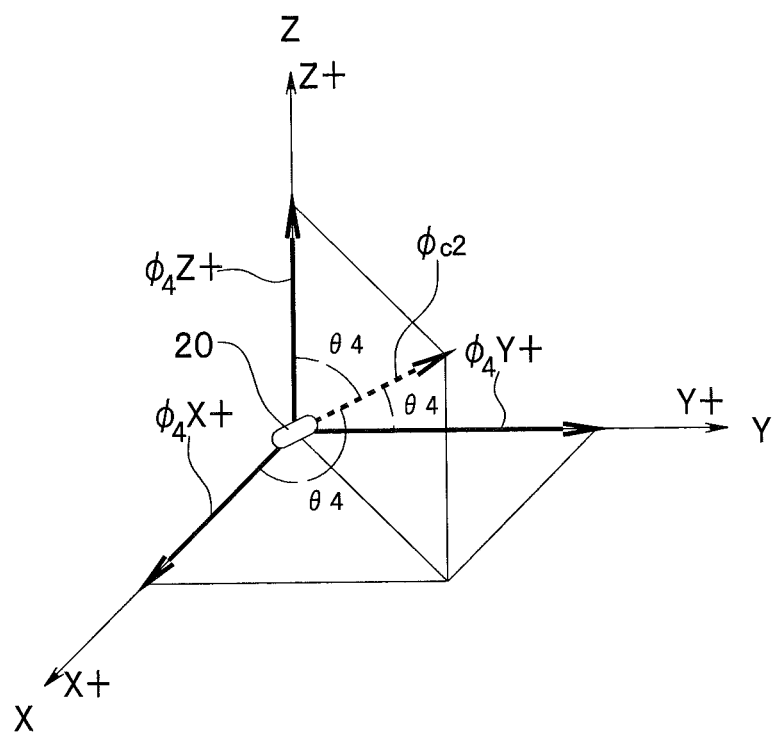
FIG. 9 is a view that illustrates an example in a case where a capsule-type endoscope is facing in a direction that corresponds to the middle between all three axes of a three-dimensional orthogonal coordinate system.

Based on a detection result with respect to the orientation of the endoscope 20, the coil selection section 51 determines by calculation that the endoscope 20 is facing in a direction that corresponds to the middle between the X-axis, the Y-axis, and the Z-axis of the three-dimensional orthogonal coordinate system. More specifically, based on the detection result with respect to the orientation of the endoscope 20, the coil selection section 51, for example, as shown in FIG. 9, detects that the endoscope 20 forms an angle $\theta_4$ with respect to each of the X-axis, the Y-axis, and the Z-axis of the three-dimensional orthogonal coordinate system. In this connection, hereunder an example of a case in which $\theta_4=54.7°$ is described.

When it is detected that the endoscope 20 is facing in the direction shown in FIG. 9, the coil selection section 51 selects the information of "pattern 10" from among the patterns shown in FIG. 6.

Based on the information of the selected "pattern 10", the coil selection section 51 performs control to switch on the switches 70*a*, 70*f*, 70*g*, and 70*i* and switch off the switches 70*b* to 70*e*, 70*h*, and 70*j* to 70*m*.

In other words, when it is detected that the endoscope 20 is facing in the direction shown in FIG. 9, the coil selection section 51 selects the X-axis coil 44, the Y-axis coil 45, and the Z-axis coil 46 as antennas that are driving targets, and thereafter performs control with respect to each of the switches 70*a* to 70*m* so as to connect the X-axis coil 44, the Y-axis coil 45, the Z-axis coil 46, and the drive section 41 in series.

In accordance with the control of the coil selection section 51, an alternating current is applied between the terminal A and the terminal F at the drive section 41. When the current is applied between the terminal A and the terminal F at the drive section 41, the current flows on a path on which the terminal A, the switch 70*a*, the capacitor 44C, the coil 44A, the coil 44B, the switch 70*g*, the capacitor 45C, the coil 45A, the coil 45B, the switch 70*i*, the capacitor 46C, the coil 46A, the coil 46B, the switch 70*f* and the terminal F are connected in series. As a result, a magnetic field is generated between a region corresponding to a middle region between the X+ region, the Y+ region, and the Z+ region and a region corresponding to a middle region between the X− region, the Y− region and the Z− region.

More specifically, when a current flows in the order of terminal A→switch 70*a*→capacitor 44C→coil 44A→coil 44B→switch 70*g*→capacitor 45C→coil 45A→coil 45B→switch 70*i*→capacitor 46C→coil 46A→coil 46B→switch 70*f*→terminal F, as shown in FIG. 9, a combined magnetic field $\phi_{c2}$ is generated by a magnetic field $\phi_4 X+$ along the positive direction of the X-axis, a magnetic field $\phi_4 Y+$ along the positive direction of the Y-axis, and a magnetic field $\phi_4 Z+$ along the positive direction of the Z-axis. More specifically, when the coil selection section 51 selects "pattern 10", since the coil 44A, the coil 44B, the coil 45A, the coil 45B, the coil 46A and the coil 46B are connected in series, a current of the same size flows to each coil. In such a case, an electric power $P_{XYZ}$ that is consumed at the wireless power supply apparatus 10 is shown by the following equation (6).

Equation 6

$$P_{XYZ}=I_{XYZ}^2 \times Z_{XYZ} \quad (6)$$

In the above equation (6), $I_{XYZ}$ represents the current required in order to generate the combined magnetic field $\phi_{c2}$, and $Z_{XYZ}$ represents a combined impedance of the X-axis coil unit 44S, the Y-axis coil unit 45S, and the Z-axis coil unit 46S.

In this case, if it is assumed that the size of the combined magnetic field $\phi_{c2}$ is equal to the size of the aforementioned magnetic field $\phi_c$, and that $\theta_4=54.7°$, when "pattern 10" is selected by the coil selection section 51, the intensity of the magnetic field $\phi_4 X+$, the intensity of the magnetic field $\phi_4 Y+$ and the intensity of the magnetic field $\phi_4 Z+$ become equal as shown by the following equation (7).

Equation 7

$$\phi_4 X+ = \phi_4 Y+ = \phi_4 Z+ = \phi_c \times 1/\sqrt{3} \quad (7)$$

Therefore, the size of a current $I_{XYZ}$ that flows to the coil 44A, the coil 44B, the coil 45A, the coil 45B, the coil 46A, and the coil 46B that are connected in series is shown by the following equation (8).

Equation 8

$$I_{XYZ}=I_{X1} \times 1/\sqrt{3} \quad (8)$$

In addition, if it is assumed that the respective impedances of the Y-axis coil unit 45S and the Z-axis coil unit 46S are equal to the impedance $Z_{X1}$ of the X-axis coil unit 44S, the above described equation (6) accordingly changes into equation (9) below.

Equation 9

$$\begin{aligned} P_{XYZ} &= I_{XYZ}^2 \times Z_{XYZ} \quad (9) \\ &= \left(I_{X1} \times 1/\sqrt{3}\right)^2 \times 3 \times Z_{X1} \\ &= I_{X1}^2 \times Z_{X1} = P_{X1} \end{aligned}$$

In contrast, when the endoscope 20 is facing in a direction that corresponds to the middle between the X-axis, the Y-axis, and the Z-axis of the three-dimensional orthogonal coordinate system, aside from the aforementioned "pattern 10", the coil selection section 51 of the wireless power supply apparatus 10 of the present embodiment selects a single pattern that is most suitable in accordance with the orientation of the endoscope 20 from among "pattern 11", "pattern 12", and "pattern 13" shown in FIG. 6.

When "pattern 11" is selected, the coil selection section 51 performs control so that a current flows on a path on which the terminal A, the switch 70a, the capacitor 44C, the coil 44A, the coil 44B, the switch 70g, the capacitor 45C, the coil 45A, the coil 45B, the switch 70j, the coil 46B, the coil 46A, the capacitor 46C, the switch 70e, and the terminal E are connected in series. As a result, a magnetic field that is in accordance with the current is generated.

Further, when "pattern 12" is selected, the coil selection section 51 performs control so that a current flows on a path on which the terminal A, the switch 70a, the capacitor 44C, the coil 44A, the coil 44B, the switch 70k, the capacitor 46C, the coil 46A, the coil 46B, the switch 70j, the coil 45B, the coil 45A, the capacitor 45C, the switch 70c, and the terminal C are connected in series, and thereafter a magnetic field that is in accordance with the current is generated.

Further, when "pattern 13" is selected, the coil selection section 51 performs control so that a current flows on a path on which the terminal A, the switch 70a, the capacitor 44C, the coil 44A, the coil 44B, the switch 70m, the coil 46B, the coil 46A, the capacitor 46C, the switch 70i, the coil 45B, the coil 45A, the capacitor 45C, the switch 70c, and the terminal C are connected in series, and thereafter a magnetic field that is in accordance with the current is generated. In other words, the coil selection section 51 selects all of the three sets of power transmission coils and connects the three sets of power transmission coils in series.

More specifically, when the wireless power supply apparatus 10 according to the present embodiment selects any one of "pattern 11", "pattern 12", and "pattern 13", operations are performed in a similar manner to the operations when the aforementioned "pattern 10" is selected. Consequently, according to the wireless power supply apparatus 10 of the present embodiment, when the same conditions as in the case of the aforementioned "pattern 10" are set, the above described equations (6) to (9) can be similarly applied with respect to any of "pattern 11", "pattern 12", and "pattern 13".

As described above, when the endoscope 20 is facing in a direction that corresponds to the middle between all three axes of the three-dimensional orthogonal coordinate system, the wireless power supply apparatus 10, the power transmission coil unit 49, and the wireless power supply system 1 serially connect power transmission antennas that are respectively disposed along the three axes and cause a current to flow. Therefore, the wireless power supply apparatus 10 of the present embodiment can cause the axial direction of the endoscope 20 and a direction in which a magnetic field is generated to match while suppressing power consumption, and can thus supply electric power efficiently to the endoscope 20.

More specifically, since the wireless power supply apparatus 10 has the coil selection section 51 that selects at least one of the power transmission coils 44, 45, and 46 for causing the power receiving coil 21 of the endoscope 20 to efficiently generate an induced voltage regardless of which direction the endoscope 20 is facing, the wireless power supply apparatus 10 can efficiently supply electric power.

Note that the present embodiment is not limited to a case in which the endoscope 20 is disposed at a position corresponding to the origin of a three-dimensional orthogonal coordinate system, and the present embodiment can be applied in an approximately similar manner in a case in which the endoscope 20 is disposed at another position within a three-dimensional orthogonal coordinate system.

Further, the wireless power supply apparatus 10 of the present embodiment is not limited to an apparatus in which power transmission coils are disposed along three axes, namely, the X-axis, the Y-axis, and the Z-axis, of a three-dimensional orthogonal coordinate system, and may be an apparatus in which a power transmission coil is disposed along another axis other than the aforementioned three axes, or may be an apparatus in which a power transmission coil is disposed along each axis in a coordinate system other than a three-dimensional orthogonal coordinate system.

As described above, a wireless power supply apparatus of an embodiment of the present invention wirelessly supplies power to a capsule-type medical device that is introduced into the body of an individual to be examined, wherein: the capsule-type medical device has a power receiving coil that receives an electric power by means of a change in a magnetic field in a longitudinal direction thereof; the wireless power supply apparatus including: a power transmission coil unit that is arranged on the individual to be examined and that has three sets of power transmission coils that generate the magnetic field in directions that are orthogonal to each other, drive means that applies an electric current to at least one set of the power transmission coils, and coil selection means that selects the power transmission coils to apply the electric current to in order to generate a magnetic field in a longitudinal direction of the capsule-type medical device.

<Second Embodiment>

A wireless power supply apparatus 10A and a wireless power supply system 1A according to a second embodiment of the present invention are described hereunder with reference to the drawings. Since the wireless power supply apparatus 10A and the wireless power supply system 1A of the present embodiment are similar to the wireless power supply apparatus 10 and the wireless power supply system 1 of the first embodiment, like components are denoted by like reference symbols and a description of such components is omitted below.

FIG. 10 is a configuration diagram that illustrates the configuration of the wireless power supply apparatus 10A of the second embodiment. A power transmission coil unit 49A of the wireless power supply system 1A of the present embodiment has a gravity sensor 16. The gravity sensor 16 is a sensor that detects a gravitational direction, for example, a triaxial acceleration sensor.

The center of gravity of a capsule-type endoscope 20A that receives an electric power from the wireless power supply apparatus 10A of the present embodiment is eccentric to the rear end side in the longitudinal direction (LD), in other words, an end portion side on a side opposite to the CCD 23, and the overall specific gravity thereof is less than water. Therefore, as described later, the endoscope 20A floats with a longitudinal direction thereof being perpendicular to a surface of a retained liquid. In order to obtain a weight balance with an eccentric center of gravity, in the endoscope 20A, for example, the secondary battery 24 that is a comparatively heavy component may be disposed on the rear end side or an unshown deadweight may be disposed on the rear end side.

The coil selection section 51 of the wireless power supply apparatus 10 of the first embodiment performed monitoring and control of the position and orientation of the endoscope 20 using technology disclosed in Japanese Patent Application Laid-Open Publication No. 2005-304638. In contrast, a coil selection section control section 51A of the wireless power supply apparatus 10A of the present embodiment selects and controls a Helmholtz coil that generates a magnetic field in a parallel direction to a gravitational direction that is detected by the gravity sensor 16 of the power transmission coil unit 49A. More specifically, for example, as shown in FIG. 2, when the individual to be examined 39 is in an upright posture, since the gravitational direction is the Z-axis direction, the coil selection section control section 51A selects the coil 46. In this case, the term "coil that generates a magnetic field in a parallel direction to a gravitational direction", that the coil selection section control section 51A selects, refers to a coil that generates a magnetic field in a direction closest to a direction that is parallel to the gravitational direction among the three sets of power transmission coils 44, 45, and 46.

Next, the operations of the wireless power supply apparatus 10A will be described using FIG. 11A to FIG. 13B.

First, prior to observation, the individual to be examined 39 puts on the power transmission coil unit 49A in a vest shape. Further, a reception antenna and a reception apparatus main body for receiving a signal from the endoscope 20A are disposed at a predetermined position in the vicinity of the individual to be examined 39. Subsequently, the endoscope 20A is introduced into a stomach 30A inside the body of the individual to be examined 39 by causing the individual to be examined 39 to swallow the endoscope 20A together with a liquid, for example, water 31. In this connection, a liquid for causing the endoscope 20A to float is not limited to water and may be any liquid that is not harmful to the individual to be examined 39.

Although it is not essential for the endoscope 20A to be swallowed at the same time as the water 31, swallowing the endoscope 20A and the water 31 together facilitates swallowing of the endoscope 20A. Thereafter, the physician or the like waits a few minutes to allow the liquid surface 31A inside the stomach 30A to stabilize before continuing.

Figure 11A:
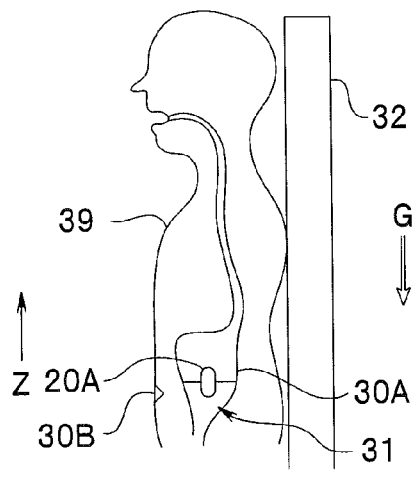
Figure 11B:
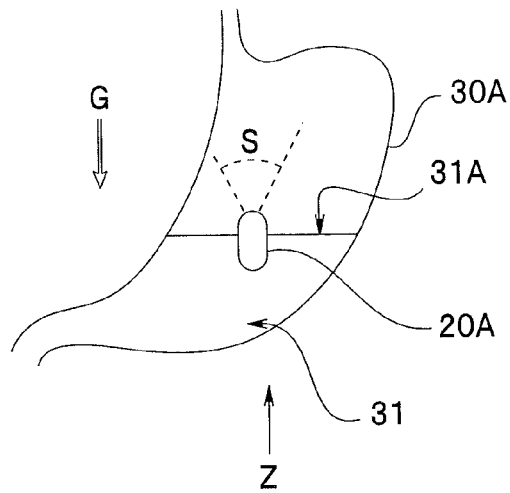

As shown in FIG. 11A and FIG. 11B, when the individual to be examined 39 is in an upright posture, a field of view S of the CCD 23 of the endoscope 20A which is floating with a longitudinal direction thereof being perpendicular to a surface of the water 31 that is retained inside the stomach 30A is facing the upper portion of the stomach 30A. Hence, images of the upper portion (cardiac region) of the stomach 30A can be picked up.

Subsequently, the coil selection section control section 51A of the wireless power supply apparatus 10A selects the Z-axis coil 46 that generates a magnetic field in the gravitational direction, and the drive section 41 applies an alternating current to the coil 46. Since the magnetic path direction of the power receiving coil 21 is the longitudinal direction of the endoscope 20A, the magnetic path direction matches a gravitational direction G that is detected by the gravity sensor 16, and hence the power receiving coil 21 can receive an electric power by means of a magnetic induction effect produced by a magnetic field that the Z-axis coil 46 generates.

Figure 12A:
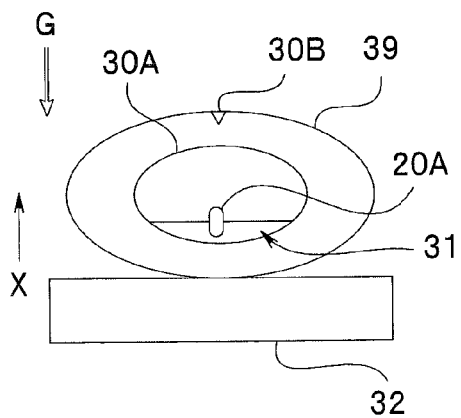
Figure 12B:
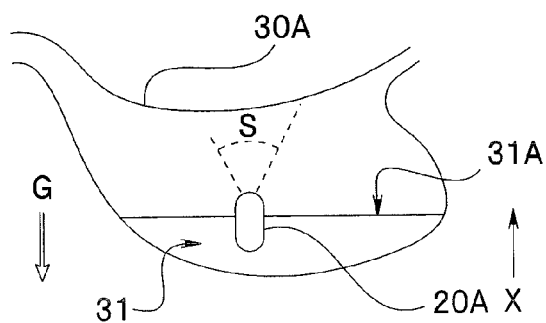

Next, as shown in FIG. 12A and FIG. 12B, when the individual to be examined 39 is in a supine posture, since the field of view S of the CCD 23 of the endoscope 20A which is floating with a longitudinal direction thereof being perpendicular to a surface of the water 31 that is retained inside the stomach 30A is facing a front side of the stomach 30A, that is, a navel 30B side, images of the front side of the stomach 30A can be picked up. In this connection, to change the posture from an upright position to a supine position, for example, a posture changing device 32 may be used, or the individual to be examined 39 may change their body position by themselves.

Subsequently, the coil selection section control section 51A of the wireless power supply apparatus 10A selects the X-axis coil 44 that generates a magnetic field in the gravitational direction G, and the drive section 41 applies an alternating current to the X-axis coil 44. Since the magnetic path direction of the power receiving coil 21 is the longitudinal direction of the endoscope 20A, the magnetic path direction matches the gravitational direction G that is detected by the gravity sensor 16, and hence, the power receiving coil 21 can receive an electric power by means of a magnetic induction effect produced by a magnetic field that the X-axis coil 44 generates.

Figure 13A:
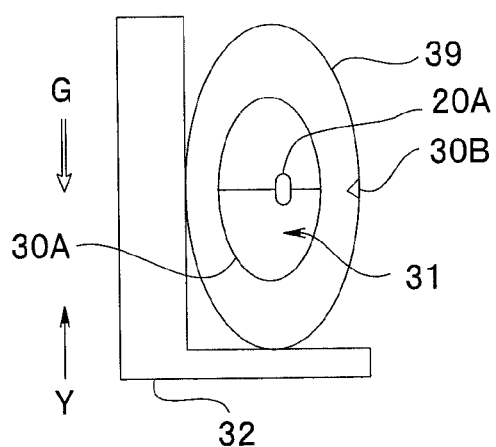
Figure 13B:
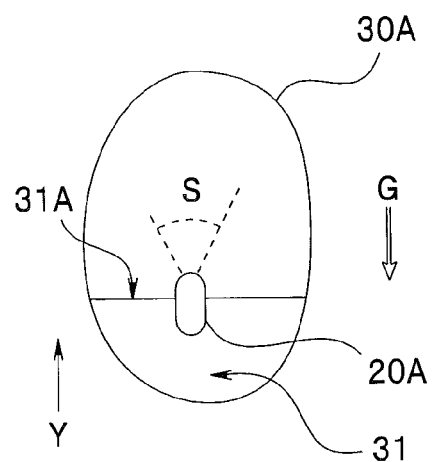

Next, as shown in FIG. 13A and FIG. 13B, when the individual to be examined 39 is in a lateral posture in which the right side of the individual to be examined 39 is the bottom side, since the field of view S of the CCD 23 of the endoscope 20A which is floating with a longitudinal direction thereof being perpendicular to a surface of the water 31 that is retained inside the stomach 30A is facing a left side of the stomach 30A, images of the left side of the stomach 30A can be picked up. In this connection, to change the posture from a supine position to a lateral position, for example, the posture changing device 32 may be used, or the individual to be examined 39 may change their body position by themselves.

Subsequently, the coil selection section control section 51A of the wireless power supply apparatus 10A selects the Y-axis coil 45 that generates a magnetic field in the gravitational direction G, and the drive section 41 applies an alternating current to the Y-axis coil 45. Since the magnetic path direction of the power receiving coil 21 is the longitudinal direction of the endoscope 20A, the magnetic path direction matches the gravitational direction G that is detected by the gravity sensor 16, and hence the power receiving coil 21 can receive an electric power by means of a magnetic induction effect produced by a magnetic field that the Y-axis coil 45 generates.

In addition, when the individual to be examined 39 is in a prone position in which the front side of the individual to be examined 39 is facing downward, since the field of view S of the CCD 23 of the endoscope 20A which is floating with a longitudinal direction thereof being perpendicular to a surface of the water 31 that is retained inside the stomach 30A is facing the rear surface of the stomach 30A, images of the rear surface of the stomach 30A can be picked up. When the individual to be examined 39 is in the prone position, the coil selection section control section 51A of the wireless power supply apparatus 10A selects the X-axis coil 44 that generates a magnetic field in the gravitational direction G, and the drive section 41 applies an alternating current to the X-axis coil 44. Since the magnetic path direction of the power receiving coil 21 is the longitudinal direction of the endoscope 20A, the magnetic path direction matches the gravitational direction G that is detected by the gravity sensor 16, and hence the power receiving coil 21 can receive an electric power by means of a magnetic induction effect produced by a magnetic field that the X-axis coil 44 generates.

Further, when the individual to be examined 39 is in a lateral posture in which the left side of the individual to be examined 39 is the bottom side, since the field of view S of the CCD 23 of the endoscope 20A which is floating with a longitudinal direction thereof being perpendicular to a surface of the water 31 that is retained inside the stomach 30A is facing a right side of the stomach 30A, images of the right side of the stomach 30A can be picked up. The coil selection section control section 51A of the wireless power supply apparatus 10A selects the Y-axis coil 45 that generates a magnetic field in the gravitational direction G, and the drive section 41 applies an alternating current to the Y-axis coil 45. Since the magnetic path direction of the power receiving coil 21 is the longitudinal direction of the endoscope 20A, the magnetic path direction matches the gravitational direction G that is detected by the gravity sensor 16, and hence the power receiving coil 21 can receive an electric power by means of a magnetic induction effect produced by a magnetic field that the Y-axis coil 45 generates.

More specifically, it is possible for the endoscope 20A to acquire image information of the entire gastric wall of the stomach 30A by changing the posture of the individual to be examined 39. Further, since the wireless power supply apparatus 10A, the power transmission coil unit 49A, and the wireless power supply system 1A of the present embodiment can effectively switch a coil to be driven in accordance with a change in the posture of the individual to be examined 39 based on the gravitational direction G that is detected by the gravity sensor 16 of the power transmission coil unit 49A and thereby generate a magnetic field, the advantages of the wireless power supply apparatus 10 and the like of the first embodiment can be realized with a simple configuration.

As described above, the power transmission coil unit 49A of the present embodiment is a power transmission antenna of a wireless power supply apparatus that wirelessly supplies power to a capsule-type medical device that is introduced into a body of an individual to be examined, wherein: the capsule-type medical device has a power receiving coil that receives an electric power by means of a change in a magnetic field in a longitudinal direction thereof, and has a structure that enables the capsule-type medical device to float with a longitudinal direction thereof being perpendicular to a surface of a liquid that is retained inside a stomach of the individual to be examined; the power transmission coil unit 49A has three sets of power transmission coils that generate the magnetic field in directions that are orthogonal to each other, and a gravity sensor; and the power transmission coil unit 49A is arranged in clothing that the individual to be examined wears.

<Supplementary Explanation>

Although a case in which any one set of power transmission coils is selected is exemplified in the above description, as described in the first embodiment, even in a case in which the most suitable two sets or three sets of power transmission coils are selected depending on the gravitational direction that the gravity sensor 16 detects, since the wireless power supply apparatus 10A and the like of the present embodiment connect the selected power transmission coils in series and apply a current, the supply of power can be performed efficiently.

In this connection, although the power transmission coils 44 to 46 of the present embodiment and a modification example as described above are Helmholtz-type coils in which two coils are disposed facing each other, the respective power transmission coils 44 to 46 may be a solenoid-type coil that is constituted by a single coil.

Further, although an example of the capsule-type endoscope 20 that has one CCD 23 is described above, the capsule-type endoscope may have image pickup means at each of the two end portions in the longitudinal direction. Furthermore, the present invention is not limited to a capsule-type endoscope that has image pickup means, and can be applied to various kinds of capsule-type medical devices such as a capsule-type medical device for collecting digestive fluids, a swallowable pH sensor, or a drug delivery system.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A wireless power supply apparatus that wirelessly supplies power to a capsule-type medical device that is introduced into a body of a subject, wherein:
    the capsule-type medical device has a power receiving coil that receives an electric power by means of a change in a magnetic field;
    the wireless power supply apparatus comprising:
    a power transmission coil unit that is arranged on the subject, and that has three sets of power transmission coils that generate the magnetic field in directions that are orthogonal to each other,
    a drive section that applies an electric current to at least one set of the power transmission coils, and
    a coil selection section that selects the power transmission coils to apply the electric current to in order to cause the power receiving coil of the capsule-type medical device to generate an induced voltage.

2. The wireless power supply apparatus according to claim 1, wherein when two sets or more of the power transmission coils are selected, the coil selection section serially connects the two sets or more of the power transmission coils that are selected.

3. The wireless power supply apparatus according to claim 2, wherein the power transmission coils are arranged in clothing that the subject wears.

4. The wireless power supply apparatus according to claim 3, wherein:
the capsule-type medical device has a structure that enables the capsule-type endoscope to float with a longitudinal direction thereof being perpendicular to a surface of a liquid that is retained inside a stomach of the subject;
the power transmission coil unit has a gravity sensor that detects a gravitational direction; and
the coil selection section selects the power transmission coils by taking a gravitational direction that the gravity sensor detects to be the longitudinal direction of the capsule-type medical device.

5. The wireless power supply apparatus according to claim 4, wherein the gravity sensor is a triaxial acceleration sensor.

6. The wireless power supply apparatus according to claim 5, wherein the capsule-type medical device is a capsule-type endoscope that has an image pickup section that is arranged at an end portion in the longitudinal direction.

7. A power transmission coil unit of a wireless power supply apparatus that wirelessly supplies power to a capsule-type medical device that is introduced into a body of a subject, wherein:
the capsule-type medical device has a power receiving coil that receives an electric power by means of a change in a magnetic field, and has a structure that enables the capsule-type medical device to float with a longitudinal direction thereof being perpendicular to a surface of a liquid that is retained inside a stomach of the subject;
the power transmission coil unit comprises three sets of power transmission coils that generate the magnetic field in directions that are orthogonal to each other, and a gravity sensor that detects a gravitational direction; and
the power transmission coil unit is arranged in clothing that the subject wears.

8. The power transmission coil unit according to claim 7, wherein the gravity sensor is a triaxial acceleration sensor.

9. The power transmission coil unit according to claim 8, wherein two sets or more of the power transmission coils are connected in series by coil a selection section of the wireless power supply apparatus.

10. The power transmission coil unit according to claim 9, wherein the capsule-type medical device is a capsule-type endoscope that has an image pickup section that is arranged at an end portion in a longitudinal direction.

11. A wireless power supply system comprising a capsule-type medical device that is introduced into a body of a subject, and a wireless power supply apparatus that wirelessly supplies power to the capsule-type medical device, wherein:
the capsule-type medical device is a capsule-type endoscope that has:
a power receiving coil that receives an electric power by means of a change in a magnetic field in a parallel direction to a longitudinal direction thereof, and
an image pickup section that is arranged at an end portion in the longitudinal direction; and
the wireless power supply apparatus comprises:
a power transmission coil unit that is arranged on the subject, and that has three sets of power transmission coils that generate the magnetic field in directions that are orthogonal to each other,
a drive section that applies an electric current to at least one set of the power transmission coils, and
a coil selection section that selects the power transmission coils to apply the electric current to in order to generate a magnetic field in a longitudinal direction of the capsule-type medical device.

12. The wireless power supply system according to claim 11, wherein:
when two sets or more of the power transmission coils are selected, the coil selection section serially connects the two sets or more of the power transmission coils that are selected.

13. The wireless power supply system according to claim 12, wherein the power transmission coil unit is arranged in clothing that the subject wears.

14. The wireless power supply system according to claim 13, wherein:
the capsule-type medical device has a structure that enables the capsule-type medical device to float with a longitudinal direction thereof being perpendicular to a surface of a liquid that is retained inside the body of the subject;
the power transmission coil unit has a gravity sensor that detects a gravitational direction; and
the coil selection section selects the power transmission coils by taking a gravitational direction that the gravity sensor detects to be the longitudinal direction of the capsule-type medical device.

15. The wireless power supply system according to claim 14, wherein the capsule-type medical device is a capsule-type endoscope that has an image pickup means that is arranged at an end portion in the longitudinal direction.

* * * * *